United States Patent [19]

Milkowski et al.

[11] 3,998,809
[45] Dec. 21, 1976

[54] BENZODIAZEPINE DERIVATIVES

[75] Inventors: Wolfgang Milkowski, Burgdorf; Renke Budden, Peine; Siegfried Funke, Hannover; Rolf Huschens, Hannover; Hans-Günther Liepmann, Hannover; Werner Stühmer, Eldagsen; Horst Zeugner, Hannover, all of Germany

[73] Assignee: Kali-Chemie Aktiengesellschaft, Hannover, Germany

[22] Filed: May 1, 1973

[21] Appl. No.: 355,986

[30] Foreign Application Priority Data

May 3, 1972 Germany ............................ 2221558

[52] U.S. Cl. ................ 260/239 BD; 260/247.1 L; 260/247.5 H; 260/268 BC; 260/293.59; 260/326 S; 260/326 N; 260/427; 260/490; 260/558 R; 260/558 S; 260/558 D; 260/559 R; 260/570.6; 260/559 S

[51] Int. Cl.$^2$ ............. C07D 243/16; C07D 401/06; C07D 403/06; C07D 413/06

[58] Field of Search ...... 260/340.3, 239 BD, 247.5, 260/268 BC, 293.59, 326 N, 326.5 CA, 326.81

[56] References Cited

OTHER PUBLICATIONS

Field et al., J. Org. Chem., vol. 30, pp. 2098–2100 (1965).
Santilli et al., J. Org. Chem., vol. 30, pp. 2100–2102 (1965).
Hoffmann-LaRoche, Chem. Abstracts, vol. 65, columns 15407–15408 (1966).

*Primary Examiner*—Alton D. Rollins
*Attorney, Agent, or Firm*—Michael J. Striker

[57] ABSTRACT

A benzodiazepine derivative of the formula

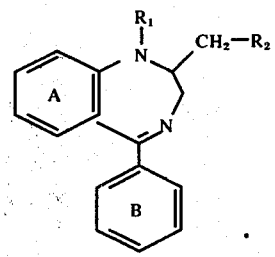

wherein
$R_1$ is hydrogen, lower alkyl which may be a straight chain, branched chain or cyclic group and may also be substituted,
$R_2$ is halogen, free hydroxyl, esterified hydroxyl, etherified hydroxyl, nitrile, carboxyl or a derivative thereof or is thioalkyl, thioaryl or the group

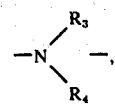

$R_3$ and $R_4$ in this group being the same or different and being hydrogen, acyl, aryl, alkyl, aralkyl, aryloxyalkyl which latter five groups may also be substituted, or wherein $R_3$ and $R_4$ are saturated or unsaturated, straight chain or branched alkyl and in which groups the several alkyl may be interconnected directly or through a hetero atom, which if the hetero atom is nitrogen may also be substituted,
and in which formula I, A and B are phenyl or phenyl substituted by nitro, trifluoromethyl, halogen, methylthio alkyl or alkoxy;
or a pharmaceutically acceptable acid addition salt of said benzodiazepine derivatives of formula I.

22 Claims, No Drawings

BENZODIAZEPINE DERIVATIVES

Benzo-1,4-diazepines have been disclosed in the literature as valuable pharmaceutical compounds, see Burger, Medicinal Chemistry, (1970), part 2, third edition.

However, the benzo-1,4-diazepines of the formula shown in the abstract above and in claim 1, to applicants' knowledge, have nowhere been disclosed so far.

Lower alkyl in these compounds identified by $R_1$ may for instance be methyl, ethyl, propyl, isopropyl, butyl, sec.-butyl, tert.-butyl, amyl, hexyl, cyclopentyl, cyclohexyl or cyclopropylmethyl. $R_1$ can also be an aromatic substituted alkyl residue or an alkyl residue which is substituted with a free esterified or etherified hydroxyl group. The benzene rings A and B may include one or several identical or different substituents, for instance, nitro, trifluormethyl, halogen (chlorine, bromine, fluorine and iodine), methylthis alkyl (such as methyl, ethyl, propyl, isopropyl, butyl or sec.-butyl) or alkoxy (such as methoxy, ethoxy, propoxy or butoxy). Lower alkyl groups as such and in combined groups may have from 1 to 10 carbon atoms.

UTILITY AND TESTS

The compounds of the invention are in particular useful in their action on the central nervous system. They have an anticonvulsive, sedative, muscle relaxant and tranquilizer effect.

They can be used with the usual pharmaceutically acceptable diluents or carrier materials such as cellulose, starch, polyethylene glycol, magnesium stearate or talcum. Water-soluble compounds can also be administered as aqueous solutions.

The dosage depends on age, body weight and condition of the patient. Preferred is a dose of 1 to 200 mg per day per kg. of body weight. The amount may be administered as a single dose per day or may be spread throughout the day. Normally smaller doses are used in case of parenteral administration.

The main use of the compounds is as tranquilizers with only small musculotropic properties in the treatment of mental afflictions. They can be administered per os or parenterally to human patients and animals.

The following tests have been carried out with animals. The compounds are particularly distinguished by their excellent compatibility (therapeutic index) when compared with the normal commercial products.

The tests were carried out to determine the following action of the compounds.

1. Tests regarding anticonvulsive activity:

a. Electroshock attacks:

The test substances as appearing from the Table further below were administered per os to groups of five mice each at a logarithmic dosage spacing of 0.1673 [Hackenberg, U. and H. Bartling, Naunyn-Schmiedeberg's Arch. exp. Path. u. Pharmak. 235, 437–463 (1959)]. One hour after application the electrodes were attached to the ears of the animals and the electrical shock or stimulus was applied. The appearance or absence of tonic extensor attacks was recorded and the percentage of protective action against the attacks was determined.

b. Pentetrazole spasm:

The test substances as listed below were applied to groups of 10 mice each per os and likewise at a logarithmic spacing of the dosage by 0.1673. Sixty minutes after application pentetrazole (pentylenetetrazole) was injected subcutaneously at a dosage of 100 mg/kg. The appearance of clonic and tonic convulsions and death was observed during a time of 45 minutes. The total observation time was up to 3 hours. The protective effect against convulsion and death was determined by comparison in simultaneously performed tests with control animals. The effective dose $ED_{50}$ against convulsions was determined from the probability logarithmic dosage curves.

2. Test regarding antiaggressive action in an electrically irritated fighter mouse:

The method is described in Tedeschi, R.E. et al. J. Pharmacol. Exptl. Therap. 125, 28 (1959). One hour after application per os of the test compounds eight pairs of mice per dose were tested by the mentioned method regarding the aggression properties. The logarithmic dosage spacing was likewise 0.1673. The time of the stimulation was 3 minutes.

3. Test regarding anesthesia potentiating properties after application of hexobarbital:

The method involved again the administration of the test substances at a logarithmic dose spacing per os of 0.3324. Thirty minutes after application hexobarbital was applied at a dose of 65 mg/kg by intravenous application. The duration of the sleeping time was determined. $ED_{50}$ was taken as equal to 30 minutes in side position.

4. Acute toxicity:

The acute toxicity was determined after a single application per os in white NMRI mice which had not been fed. The calculation was effected by the method of Litchfield, J. T. and F. Wilcoxon, J. Pharmacol. Exptl. Therap. 96 99 (1949).

The test results appear from the following Table.

TABLE 1

| | TESTS REGARDING ACTIVITY (ALL AMOUNTS IN mg/kg) | | | | |
|---|---|---|---|---|---|
| | $LD_{50}$ per os | Electroshock p.o. $ED_{50}$ | Pentetrazole-spasm p.o. $ED_{50}$ | Fighter mouse p.o. $ED_{50}$ | Anaesthesia p.o. $ED_{50}$ |
| 7-chloro-1-methyl-2-acetylaminomethyl-5-phenyl-2,3-dihydro-1H-1,4-benzodiazepine hydrochloride | 1280 | 215 | 180 | 82 | 30 |
| 7-chloro-1-methyl-2-isopropylcarboxamidomethyl-5-phenyl-2,3-dihydro-1H-1,4-benzodiazepine hydrochloride | 1136 | 36 | 19 | 48 | 30 |
| 7-chloro-1-methyl-2-methoxymethyl-5-(2-chlorophenyl)-2,3-dihydro-1H-1,4- | | | | | |

TABLE 1-continued

TESTS REGARDING ACTIVITY (ALL AMOUNTS IN mg/kg)

| | $LD_{50}$ per os | Electroshock p.o. $ED_{50}$ | Pentetrazole-spasm p.o. $ED_{50}$ | Fighter mouse p.o. $ED_{50}$ | Anaesthesia p.o. $ED_{50}$ |
|---|---|---|---|---|---|
| benzodiazepine hydrochloride | >1470 | 46 | 2.2 | 45 | 1.6 |
| 7-chloro-1-methyl-2-hydroxymethyl-5-(2-chlorophenyl)-2,3-dihydro-1H-1,4-benzodiazepine | 4640 | 46.4 | 13.2 | 46 | 2.0 |

MAKING OF STARTING MATERIALS

The compounds of the invention of formula I are made by starting from acyldiamines of the formula

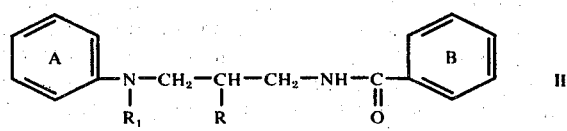

wherein A, B and $R_1$ have the same meaning as given in the abstract and below in claim 1 in connection with formula I and wherein R is a free or esterified hydroxyl group.

These compounds are themselves novel and form part of the present invention. They can be made by reacting a diamine of the formula

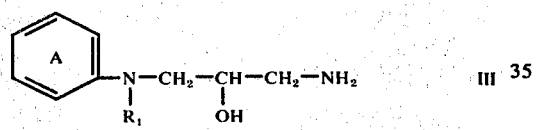

in which A and $R_1$ have the meaning as just given with a carboxylic acid derivative in a suitable solvent which acid derivative should be adapted to form carboxylic acid amides and -esters. As carboxylic acid derivatives of this type can particularly be used carboxylic acid esters, carboxylic acid anhydrides, mixed carboxylic acid anhydrides and carboxylic acid halides.

The reaction can be carried out in an inert solvent in the presence of an acid acceptor (acid binding reagent). As such there are particularly suitable tertiary amines, such as, triethylamine or pyridine. If the acid binding reagent is used in an excess it can also be employed as the solvent for the reaction. The reaction can however also be carried out in the absence of an acid binding reagent by using an inert solvent. Such inert solvents are for instance methylene chloride, chloroform, acetone, dioxane, benzene, toluene, chlorobenzene, etc. The temperature of the reaction is determined by the type of carboxylic acid derivative and is between −30° C and the boiling point of the particular solvent. The reaction can be carried out at atmospheric pressure but also at an elevated pressure.

If the reaction is carried out by using equimolar amounts there are in preference obtained amides of the above formula II wherein R is OH. The hydroxyl group in these compounds can, if desired, be esterified with suitable carboxylic acid derivatives, such as, carboxylic acid anhydrides, -esters or -chlorides. Upon use of two mols of the particular carboxylic acid derivative per mol of diamine an esterification of the hydroxyl group occurs simultaneously with the amide formation. If compounds of the formula III above in which $R_1 =$ H are reacted with three mols of a suitable carboxylic acid derivative, triacyl derivatives are obtained.

PROCESS OF MAKING THE COMPOUNDS I OF THE INVENTION

The acyldiamines of formula II can be converted to the benzodiazepine derivatives I by different methods.

The benzodiazepine derivatives of formula I can be obtained in the first place by subjecting an acyldiamine of formula

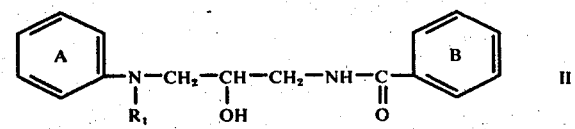

wherein A, B, and $R_1$ have the meaning as above or an acid addition salt of such acyldiamine, to the action of a ring closure (cyclization) agent at a temperature between 100° and 150° C. The ring closure agent can for instance be a phosphorus oxyhalide, preferably phosphorus oxychloride which may be used by itself or in admixture with phosphorus pentoxide or phosphorus pentoxide. There is then obtained the desired compound of formula

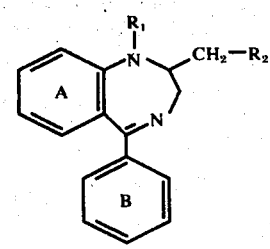

wherein $R_1$, A and B have the meaning as above and wherein $R_2$ is halogen, particularly chlorine or bromine.

This compound can then be further converted into the benzodiazepine derivatives wherein $R_2$ has the meaning other than halogen as given in the abstract and in claim 1 below. Below the cyclization temperature it is possible to isolate intermediate products in the form of acyldiamines of the above formula II in which the hydroxyl group however is substituted by halogen.

The cyclization can also be carried out with phosphorus oxyhalides in the presence of an organic base such as for instance triethylamine.

The cyclization agent can be used as the solvent in the ring closure action. The reaction is carried out at an elevated temperature, preferably at a temperature between 110° and 130° C. After completion of the reaction it is possible to further treat the reaction product in conventional form and for instance to isolate the product as a base or in the form of a pharmaceutically acceptable salt with an inorganic or organic acid, such as, the hydrochloride, sulfate, nitrate or maleate. The crude base can for instance be obtained from the reaction product by extraction with suitable solvents, for instance chloroform and concentration by evaporation of the extract. The purification of the crude base can be carried out as customary by means of active charcoal or aluminumoxide.

The cyclization temperature depends also on the substituents in the A and B phenyl rings. An amide of formula II, e.g. which is substituted in ring A by alkoxy in meta-position to n requires a lower temperature than an amide substituted in the same position by H.

It was surprising and unexpected that in this manner it was possible directly to obtain the 2-halogenomethylbenzodiazepine derivatives. It should rather have been expected that the ring closure reaction would result in a cyclization to a benzodiazocine derivative of the formula IV hereinafter.

CONVERSION OF THE 2-HALOMETHYLBENZODIAZEPINES TO OTHER DERIVATIVES

The 2-halomethylbenzodiazepines of formula I can be converted thereafter into other derivatives of formula I wherein $R_2$ has a meaning as listed except halogen.

For instance the 2-halomethylbenzodiazepines can be reacted directly with amines, amides, imides, alcoholates, phenolates, cyanides, thioalcoholates, or thiophenolates. The reaction may be carried out in the presence of an inert solvent at an elevated temperature. It is also possible to obtain the desired derivatives through the intermediate of a reactive ester. The 2-hydroxymethylbenzodiazepines can be obtained by alkaline hydrolysis.

It is also possible subsequently to introduce substituents into the phenyl rings A and B of formula I. For instance substituents such as halogen or nitro can be introduced into the rings A and B of the benzodiazepine system. The 7-chloro compounds are for instance obtained with halogenating agents such as N-chlorosuccinimide while the 7-nitro compounds can be obtained with conventional nitrating agents such as potassium nitrate and concentrated sulfuric acid. The nitration can also be carried out by simultaneously effecting a dealkylation of the nitrogen in position I of the benzodiazepine system.

Another method for obtaining the benzodiazepine derivatives starting from acyl diamines but proceeding through benzodiazocine derivatives is the subject of a separate simultaneously filed application (Ser. No. 355,989) of the same applicants.

The compounds of the present application and the method of making them herein disclosed and claimed are further illustrated in the following examples.

The formula IV of the benzodiazocines mentioned above is as follows:

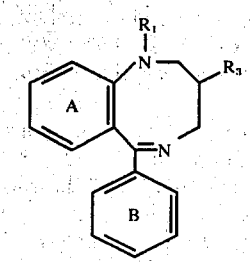

wherein $R_1$, A and B have the meaning as above and $R_3$ is is halogen or acyloxy.

Acids suitable for making the non-toxic addition salts of compounds I are e.g. acetic, propionic, diethylacetic, malonic, fumaric, maleic, lactic, tartaric, malic, citric, sulphuric, hydrobromic or orthophosphoric acid. These acid-addition salts can be used for pharmaceutical purposes like the free bases and have the advantage of being water-soluble.

EXAMPLES SHOWING MAKING OF STARTING PRODUCTS

The following examples illustrate the making of the acyldiamines of the above formula II by starting from a diamine of above formula III.

EXAMPLE 1

A solution of 128 g of N-methyl-N-(2-hydroxy-3-aminopropyl)-4'-chloroaniline in 200 ml chloroform was successively reacted with 84 ml triethylamine and 69.5 ml of benzoylchloride. The chloroform solution was washed with water after 24 hours and dried. The chloroform was then distilled off in a vacuum and the crude product was subjected to recrystallization from benzene. There were obtained 142.5 g N-methyl-N-(2-hydroxy-3-benzoylaminopropyl)-4'-chloroaniline; m.p. 136° to 137° C.

EXAMPLE 2

A solution of 59 g of N-methyl-N-(2-hydroxy-3-aminopropyl)-4'-chloraniline in 1 liter chloroform was successively reacted with 85 ml of triethylamine and 70 ml of benzoylchloride. The mixture was then heated under reflux for 4 hours and further processed as described below in Example 1. The crude product was recrystallized from isopropanol. There were obtained 61 g of N-methyl-N-(2-benzoyloxy-3-benzoylaminopropyl)-4'-chloroaniline; m.p. 145° to 148° C.

EXAMPLE 3

A solution of 45.4 g of N-methyl-N-[2-hydroxy-3-(3',4',5'-trimethoxybenzoyl)-aminopropyl]-aniline in 250 ml pyridine was reacted with 250 ml of acidic acid anhydride. The solution was poured into water after 48 hours and extracted with chloroform. The chloroform solution was concentrated by evaporation in a vacuum and the residue was recrystallized from ether. There was obtained N-methyl-N-[2-acetoxy-3-(3',4',5'-trimethoxybenzoyl)-aminopropyl]-aniline; m.p. 90° to 92° C.

In the same manner as just described in Examples 1 to 3 the following compounds were made.

N-methyl-N-[2-hydroxy-3-(3',4'-dimethoxybenzoyl)-aminopropyl]-3',4'-dimethoxyaniline, (oil);

N-methyl-N-[2-hydroxy-3-(3′,4′-dimethoxybenzoyl)-aminopropyl]-3′,4′-ethylendioxyaniline, (oil);

N-methyl-N-[2-hydroxy-3-(2′-chlorobenzoyl)-aminopropyl]-3′,4′-ethylenedioxyaniline, m.p. 105° – 107° C;

N-methyl-N-(2-hydroxy-3-benzoylaminopropyl)-4′-methylthioaniline, m.p. 141° – 142° C;

N-methyl-N-[2-hydroxy-3-(2′,6′-dichlorobenzoyl)-aminopropyl]-4′-chloroaniline, (oil);

N-methyl-N-[2-hydroxy-3-(2′,3′-dichlorobenzoyl)-aminopropyl]-4′-chloroaniline, m.p. 91° – 95° C;

N-methyl-N-[2-hydroxy-3-(2′-methylbenzoyl)-aminopropyl]-4′-chloroaniline, m.p. 108° – 113° C;

N-methyl-N-[2-hydroxy-3-(2′-bromobenzoyl)-aminopropyl]-4′-chloroaniline, m.p. 118° – 123° C;

N-methyl-N-[2-hydroxy-3-(2′-nitrobenzoyl)-aminopropyl]-4′-chloroaniline, m.p. 132° – 133° C;

N-ethyl-N-(2′hydroxy-3-benzoylaminopropyl)-4′-chloroaniline, m.p. 121° – 123° C;

N-β-methoxyethyl-N-(2-hydroxy-3-benzoylaminopropyl)-4′-chloroaniline, m.p. 120° – 122° C;

N-methyl-N-[2-hydroxy-3-(3′,4′,5′-trimethoxybenzoyl)-aminopropyl]-aniline, m.p. 126° – 129° C;

N-methyl-N-(2-hydroxy-3-benzoylaminopropyl)-4′-fluoraniline, m.p. 115° – 118° C;

N-methyl-N-[2-hydroxy-3-(2′-fluoro-benzoyl)-aminopropyl]-4′-chloroaniline, m.p. 105° – 107° C;

N-methyl-N-(2-hydroxy-3-benzoylaminopropyl)-aniline, m.p. 100° – 103° C;

N-(2-hydroxy-3-benzoylaminopropyl)-4′-chloroaniline, m.p. 175° – 177° C;

N-cyclopropylmethyl-N-(2-hydroxy-3-benzoylaminopropyl)-4′-chloroaniline, m.p. 110° – 112° C;

N-methyl-N-(2-acetoxy-3-benzoylaminopropyl)-aniline, (oil);

N-methyl-N-[2-acetoxy-3-(2′-fluorobenzoyl)-aminopropyl]-4′-chloroaniline, (oil);

N-methyl-N-[2-hydroxy-3-(2′-chlorobenzoyl)-aminopropyl]-4′-chloroaniline, m.p. 113° – 115° C;

N-methyl-N-[2-hydroxy-3-(2′-trifluoromethylbenzoyl)-aminopropyl]-4′-chloroaniline, m.p. 107° – 109° C;

N-methyl-N-[2-hydroxy-3-(3′,4′-dimethoxybenzoyl)-aminopropyl]-4′-chloroaniline, m.p. 118° – 121° C;

N-methyl-N-[2-hydroxy-3-(3′,4′-dichlorobenzoyl)-aminopropyl]-4′-chloroaniline, m.p. 115° – 117° C;

N-methyl-N-(2-benzoyloxy-3-benzoylaminopropyl)-aniline, m.p. 129° – 130° C;

N-methyl-N-[2-hydroxy-3-(2′,4′-dichlorobenzoyl)-aminopropyl]-4′-chloroaniline, m.p. 98° – 99° C;

N-methyl-N-(2-hydroxy-3-benzoylaminopropyl)-4′-methylaniline, m.p. 115° C;

N-methyl-N-(2-hydroxy-3-benzoylaminopropyl)-4′-methoxyaniline, m.p. 120° C;

N-methyl-N-[2-hydroxy-3-(3′-trifluoromethylbenzoyl)-aminopropyl]-4′-chloroaniline, (oil);

N-benzyl-N-(2-hydroxy-3-benzoylaminopropyl)-4′-chloroaniline, m.p. 128° – 132° C.

EXAMPLES ILLUSTRATING MAKING OF COMPOUNDS OF FORMULA I FROM ACYLDIAMINES

The following examples illustrate the making of the compounds of the invention corresponding to formula I starting from the acyldiamines of formula II as above given.

EXAMPLE 4

205 g of N-methyl-N-(2-hydroxy-3-benzoylaminopropyl)-4′-chloroaniline were heated in 200 ml phosphorus oxychloride to 120° C for 40 hours. After cooling the mixture was poured onto ice whereupon sodium hydroxide was added for alkalization and extraction was affected with chloroform. The several chloroform extracts from repeated extraction steps were concentrated by evaporation in a vacuum. The residue was taken up in isopropanol, treated with activated carbon and reacted with an ether solution of hydrogen chloride. There were obtained 150 g of 7-chloro-1-methyl-2-chloromethyl-5-phenyl-2,3-dihydro-1H-1,4-benzodiazepine hydrochloride which amount contained 1 mol of isopropanol. By recrystallization from isopropanol two modifications were obtained with melting points of 110° – 112° C and 178° – 180° C. The NMR spectra of both modifications were identical.

EXAMPLE 5

16 g of N-methyl-N-(2-hydroxy-3-benzoylaminopropyl)-4′-chloroaniline were introduced upon cooling into 50 ml of phosphorus oxychloride and subsequently reacted with 5.5 g of triethylamine and heated for 18 hours to 115° C. After further processing the material as shown in Example 4 there were obtained 6 g of 7-chloro-1-methyl-2-chloromethyl-5-phenyl-2,3-dihydro-1H-1,4-benzodiazepine hydrochloride which was identical with the product obtained in Example 4.

The following examples illustrate the conversion of the 2-chloromethyl benzodiazepines such as for instance described in the preceding examples 4 and 5 to benzodiazepines wherein $R_2$ in the formula I has a meaning as listed but other than halogen.

EXAMPLE 6

10 g of the chloride obtained in Example 4 were heated for 14 hours under reflux with 100 ml of piperidine. The excess piperidine was then distilled off and the residue was reacted with water and extracted with chloroform. The several chloroform extracts from different extraction steps were concentrated by evaporation in a vacuum and the residue was recrystallized from ether. There were obtained 6.8 g of 7-chloro-1-methyl-2-piperidinomethyl-5-phenyl-2,3-dihydro-1H-1,4-benzodiazepine in the form of faintly yellow crystals of a melting point of 143° to 145° C.

EXAMPLE 7

70 g of the chloride obtained in Example 4 dissolved in 1 liter water and 1 liter dioxane were heated with 500 ml of a 20% concentration sodium hydroxide under reflux for 1 hour. The dioxane was then distilled off in a vacuum, the aqueous solution was extracted with chloroform and the chloroform extract was concentrated by evaporation in a vacuum. The oily residue was taken up in isopropanol and reacted with an ether solution of hydrogen chloride. There were obtained 7-chloro-1-methyl-2-hydroxymethyl-5-phenyl-2,3-dihydro-1H-1,4-benzodiazepine hydrochloride; m.p. 227° – 235° C.

EXAMPLE 8

7.5 g of the chloride obtained in Example 4 were heated with a solution of 2 g sodium in 100 ml methanol under reflux for 24 hours. Part of the methanol was then distilled off, the mixture was reacted with water and finally extracted with chloroform. Several chloroform extracts were united and concentrated by evaporation in a vacuum. The residue was taken up in benzene and filtrated over aluminum oxide (activity stage II) with benzene. The benzene eluates were collected and concentrated by evaporation. The oil which was thus obtained was dissolved in isopropanol and reacted with an ether solution of hydrogen chloride. There were obtained 3.4 g of 7-chloro-1-methyl-2-(methoxymethyl)-5-phenyl-2,3-dihydro-1; H-1,4-benzodiazepine hydrochloride; m.p. 198° – 210° C.

The following examples illustrate further obtaining 2-chloromethyl benzodiazepines in the form of their hydrochlorides.

EXAMPLE 9

5 g of N-methyl-N-(2-hydroxy-3-benzoylaminopropyl)-4'-fluoroaniline were heated with 5 ml phosphorus oxychloride to 120° C for 27 hours. After further treating the compound as in Example 4 there was obtained 7-fluoro-1-methyl-2-chloromethyl-5-phenyl-2,3-dihydro-1H-1,4-benzodiazepine hycrochloride; m.p. 173° – 188° C.

EXAMPLE 10

4.1 g of 1-methyl-2-chloromethyl-5-phenyl-2,3-dihydro-1H-1,4-benzodiazepine and 1.94 g of N-chlorosuccinimide were heated under reflux in 50 ml methylenechloride for 24 hours. The solvent was then distilled off in a vacuum, the crude product was taken up in ether and reacted with an isopropanol solution of hydrogen chloride. There were obtained 3 g of 7-chloro-1-methyl-2-chloromethyl-5-phenyl-2,3-dihydro-1H-1,4-benzodiazepine hydrochloride. The product was identical with that of Example 4.

EXAMPLE 11

A solution of 3.7 g of 1-methyl-2-chloromethyl-5-phenyl-2,3-dihydro-1H-1,4-benzodiazepine in 20 ml glacial acetic acid and 6 ml concentrated sulfuric acid were reacted at 5° C with a solution of 3.2 g potassium nitrate in 7 ml concentrated sulfuric acid. The reaction mixture was stirred for 1 hour at room temperature, then poured onto ice, made alkaline with dilute sodium hydroxide and extracted with chloroform. The several chloroform extracts were dried and concentrated by evaporation in a vacuum. The residual oil was dissolved in isopropanol and reacted with an ether solution of hydrogen chloride. There were obtained 7-nitro-2-chloromethyl-5-phenyl-2,3-dihydro-1H-1,4-benzodiazepine hydrochloride; m.p. 213° – 214° C.

In the same manner as illustrated in Examples 4 to 11 the following compositions shown in Table 2 were made:

TABLE 2

| Substitution in phenylring A | Substitution in phenylring B | $R_1$ | $R_2$ | m.p. (° C) |
|---|---|---|---|---|
| 7-Cl | H | $CH_3$ | $OC_2H_5$ | oil |
| 7-Cl | H | $CH_3$ | i-$OC_3H_7$ | oil |
| 7-Cl | H | $CH_3$ | $C\equiv N$ | 210–214 (hydrochloride) |
| 7-Cl | H | $CH_3$ | ‒N(CH₂CH₂)₂O (morpholino) | 237–245 (dihydrochloride) |
| H | H | $CH_3$ | Cl | 195–198 (hydrochloride, contains 0.65 mol isopropanol and ½ mol water) |
| H | H | $CH_3$ | ‒N(CH₂CH₂)₂N‒$CH_3$ (N-methylpiperazino) | oil |
| 7-Cl | 2-Cl | $CH_3$ | OH | 166–168 |
| 7-Cl | 2-F | $CH_3$ | Cl | 161–165 (hydrochloride) |
| 7-Cl | 2-F | $CH_3$ | OH | 173–175 |
| 7-Cl | 2,4-di-Cl | $CH_3$ | OH | 225 (hydrochloride) |
| 7-Br | H | $CH_3$ | Cl | 95–98 (hydrochloride) |
| 7-$CH_3$ | H | $CH_3$ | Cl | 130–133 (hydrochloride, contains 1 mol isopropanol) |
| 7-$CH_3$ | H | $CH_3$ | OH | 192–195 (hydrochloride) |
| 7-$OCH_3$ | H | $CH_3$ | Cl | 191–193 (hydrochloride) |
| 7-$OCH_3$ | H | $CH_3$ | OH | 186–189 (hydrochloride) |

TABLE 2-continued

| Substitution in phenylring A | Substitution in phenylring B | R₁ | R₂ | m.p. (° C) |
|---|---|---|---|---|
| 7-Cl | 3,4-di-Cl | CH₃ | Cl | 139–141 (hydrochloride) |
| 7-Cl | 3-CF₃ | CH₃ | OH | 226–228 (hydrochloride) |
| 7-Cl | H | CH₃ | [N-methylpiperazinyl] | 214–215 (trihydrochloride, contains 1 mol ethanol) |
| 7-Cl | H | CH₃ | [phthalimido group] | 151–152 |
| 7-Cl | H | CH₃ | NH₂ | 206–209 (dihydrochloride, contains 0.5 mol isopropanol) |
| 7-Cl | H | CH₃ | —O—C(O)—C₆H₅ | 175 (after sintering from 160) (hydrochloride) |
| 7-Cl,9-NO₂ | H | H | Cl | 232–235 (hydrochloride) |
| 7-Cl | H | CH₃ | Br | oil |
| 7-Cl | H | CH₃ | —C(O)OC₂H₅ | 204–206 (hydrochloride) |
| 7-Cl | H | CH₃ | —C(O)NH₂ | 224–226 (hydrochloride) |
| 7-Cl | H | CH₃ | —S—C₆H₄—CH₃ | 185–187 (hydrochloride) |
| 7-Cl | H | CH₃ | OH (with CH₂—C₆H₅) | 208 (decomposed) (hydrochloride) |
| 7-Cl | 2-CF₃ | CH₃ | OH | 196–201 (hydrochloride) |
| 7-Cl | 2-Cl | CH₃ | CN | 171 – 174° C (hydrochloride) |
| 7-Cl | 2-Cl | CH₃ | O—CH(CH₃)₂ | 193 – 196° C (hydrochloride) |
| 7-NO₂ | H | H | Cl | 148 – 149° C |
| 9-NO₂ | H | H | Cl | 123 – 125° C |
| H | 2-Cl | CH₃ | Cl | 198 – 200° C (hydrochloride) |
| 7,9-di-NO₂ | H | H | Cl | 170 – 174° C |
| 7-Cl | H | CH₂CH₂Cl | Cl | 114 – 116° C |
| 7-Cl | H | C₂H₅ | OH | 196 – 202° C (hydrochloride) |
| 7-Cl | 2-Cl | CH₃ | COOH | 221 – 222° C (hydrochloride) |
| 7,8-di-OCH₃ | 3,4-di-OCH₃ | CH₃ | OH | 111 – 115° C (hydrochloride) |
| 7-CH₃S | H | CH₃ | Cl | oil |
| 7-Cl | 2-Cl | CH₃ | CONHCH(CH₃)₂ | 240 – 241° C (hydrochloride) |
| 7-Cl | H | CH₃ | NHCONHCH₃ | 140 – 150° C (dihydrochloride) |
| 7-Cl | H | CH₃ | NHCONH₂ | 231 – 232° C |

TABLE 2-continued

[Structure: 2,3-dihydro-1H-1,4-benzodiazepine with ring A (benzo), ring B (phenyl at 5-position), $R_1$ on N1, $CH_2-R_2$ on C2]

| Substitution in phenylring A | Substitution in phenylring B | $R_1$ | $R_2$ | m.p. (° C) |
|---|---|---|---|---|
| 7-Cl | H | $CH_3$ | $NHCONHCH(CH_3)_2$ | (hydrochloride) 180 – 182° C |
| 7-Br | H | $CH_3$ | OH | (dihydrochloride) 241 – 242° C |
| 7-F | H | $CH_3$ | OH | (hydrochloride) 99 – 101° C (hydrochloride + 1 mol isopropanol) |
| 7,8-O—$CH_2$—$CH_2$—O— | 3,4-di-$OCH_3$ | $CH_3$ | Cl | 173 – 176° C |
| 7-$CH_3$S | H | $CH_3$ | OH | 213 – 216° C (hydrochloride) |
| 7-Cl | 2,6-di-Cl | $CH_3$ | OH | 218 – 220° C (hydrochloride) |
| 7-Cl | 2,3-di-Cl | $CH_3$ | OH | 226 – 229° C (hydrochloride) |
| 7-Cl | 3,4-di-Cl | $CH_3$ | OH | 242 – 245° C (hydrochloride) |
| 7-Cl | 2-$CH_3$ | $CH_3$ | OH | 186 – 189° C (hydrochloride) |
| 7-Cl | 2-Br | $CH_3$ | OH | 205 – 206° C (hydrochloride) |
| H | 2-Cl | $CH_3$ | OH | 133 – 134° C |
| 7-Cl | 2-Cl | $CH_3$ | $OCH_3$ | 192 – 194° C (hydrochloride) |
| 7-Cl | 2-Cl | $CH_3$ | Cl | 176 – 178° C (hydrochloride) |
| 7-Cl | 2-Cl | $CH_3$ | $OC_2H_5$ | 158 – 161° C (hydrochloride) |
| 7-Cl | H | $CH_3$ | O-phenyl | 180° C (hydrochloride) |
| 7-Cl | H | $CH_3$ | O-(4-chlorophenyl) | 192 – 200° C (hydrochloride) |
| 7-Cl | H | $CH_3$ | $OCONHCH_3$ | 157 – 158° C |
| 7-Cl | H | $CH_3$ | OCONH-phenyl | 140 – 145° C |
| 7-Cl | H | $CH_3$ | $OCONHC_2H_5$ | 175 – 177° C |
| 7-Cl | H | $CH_3$ | COOH | 229° C (hydrochloride) |
| 7-Cl | H | $CH_3$ | $CONHCH(CH_3)_2$ | 220 – 223 (hydrochloride) |
| 7-Cl | H | $CH_3$ | $NHCH_2$-phenyl | 165 – 168° C (dihydrochloride) |
| 7-Cl | H | $CH_3$ | NHCO-(3,4,5-tri-$OCH_3$-phenyl) | 180° C (hydrochloride) |
| 7-Cl | H | $CH_3$ | $NHCOCH_3$ | 184 – 186° C (hydrochloride) |
| 7-Cl | H | $CH_3$ | $NHCOOC_2H_5$ | 196 – 197° C (hydrochloride) |

TABLE 2-continued

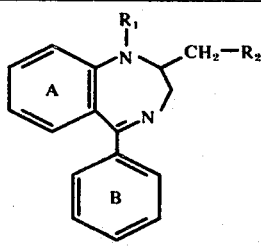

| Substitution in phenyl ring A | Substitution in phenyl ring B | $R_1$ | $R_2$ | m.p. (° C) |
|---|---|---|---|---|
| 7-Cl | H | $CH_3$ | 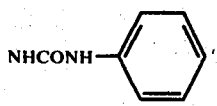 NHCONH— | 198 – 207° C (hydrochloride) |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:
1. A benzodiazepine derivative having the formula

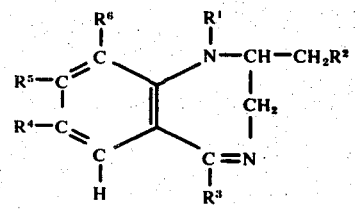

in which
$R^1$ is hydrogen, methyl, ethyl, benzyl, or 2-chloroethyl,
$R^2$ is hydroxy, alkoxy of 1 to 3 carbon atoms and being straight or branched, ethoxycarbonyl, cyano, chloro, bromo, carboxyl, amino, aminocarbonyl, methylcarbonylamino, ethoxycarbonylamino, isopropylaminocarbonyl, methylaminocarboxyl, or ethylaminocarboxyl,
$R^3$ is phenyl, 2-methylphenyl, 2-chlorophenyl, 2-fluorophenyl, 2-bromophenyl, 2-(trifluoromethyl)phenyl, 3-(trifluoromethyl)phenyl, 3,4-dimethoxyphenyl, 2,3-dichlorophenyl, 2,4-dichlorophenyl, 2,6-dichlorophenyl, or 3,4-dichlorophenyl,
$R^4$ is hydrogen, fluoro, chloro, bromo, methyl, methoxy, methylthio, or nitro,
$R^5$ is hydrogen or methoxy,
$R^6$ is hydrogen or nitro and
$R^4$ and $R^5$ together may be ethylenedioxy.

2. A compound as defined in claim 1 which is 1-methyl-2-bromomethyl-5-phenyl-7-chloro-2,3-dihydro-1H-1,4-benzodiazepine.

3. A compound as defined in claim 1 which is 1-methyl-2-cyanomethyl-5-phenyl or 5-(2-chlorophenyl)-7-chloro-2,3-dihydro-1H-1,4-benzodiazepine.

4. A compound as defined in claim 1 which is 1-methyl-2-methoxymethyl-5-phenyl or 5-(2-chlorophenyl)-7-chloro-2,3-dihydro-1H-1,4-benzodiazepine.

5. A compound as defined in claim 1 which is 1-methyl-2-ethoxymethyl-5-phenyl or 5-(2-chlorophenyl)-7-chloro-2,3-dihydro-1H-1,4-benzodiazepine.

6. A compound as defined in claim 1 which is 1-methyl-2-isopropoxymethyl-5-phenyl or 5-(2-chlorophenyl)-7-chloro-2,3-dihydro-1H-1,4-benzodiazepine.

7. A compound as defined in claim 1 which is 1-methyl-2-hydroxymethyl-5-phenyl-7-chloro-2,3-dihydro-1H-1,4-benzodiazepine.

8. A compound as defined in claim 1 which is 1-methyl-2-chloromethyl-5-(2-fluorophenyl)-7-chloro-2,3-dihydro-1H-1,4-benzodiazepine.

9. A compound as defined in claim 1 which is 1-methyl-2-hydroxymethyl-5-(2-fluorophenyl)-7-chloro-2,3-dihydro-1H-1,4-benzodiazepine.

10. A compound as defined in claim 1 which is 1-methyl-2-chloromethyl-5-phenyl-7-bromo-2,3-dihydro-1H-1,4-benzodiazepine.

11. A compound as defined in claim 1 which is 1-methyl-2-hydroxymethyl-5-(2-trifluoromethylphenyl)-7-chloro-2,3-dihydro-1H-1,4-benzodiazepine.

12. A compound as defined in claim 1 which is 1-methyl-2-chloromethyl-5-(2-chlorophenyl)-2,3-dihydro-1H-1,4-benzodiazepine.

13. A compound as defined in claim 1 which is 1-methyl-2-hydroxymethyl-5-phenyl-7-bromo-2,3-dihydro-1H-1,4-benzodiazepine.

14. A compound as defined in claim 1 which is 1-methyl-2-hydroxymethyl-5-(2-methylphenyl)-7-chloro-2,3-dihydro-1H-1,4-benzodiazepine.

15. A compound as defined in claim 1 which is 1-methyl-2-hydroxymethyl-5-(2-bromophenyl)-7-chloro-2,3-dihydro-1H-1,4-benzodiazepine.

16. A compound as defined in claim 1 which is 1-methyl-2-hydroxymethyl-5-(2-chlorophenyl)-2,3-dihydro-1H-1,4-benzodiazepine.

17. A compounds as defined in claim 1 which is 1-methyl-2-chloromethyl-5-(2-chlorophenyl)-7-chloro-2,3-dihydro-1H-1,4-benzodiazepine.

18. A compound as defined in claim 1 which is 1-methyl-2-isopropylaminocarbonylmethyl-5-phenyl or 5-(2-chlorophenyl)-7-chloro-2,3-dihydro-1H-1,4-benzodiazepine.

19. A compound as defined in claim 1 which is 7,8-ethylenedioxy-1-methyl-2-chloromethyl-5-(3,4-dimethoxyphenyl)-2,3-dihydro-1H-1,4-benzodiazepine.

20. A compound as defined in claim 1 which is 7-chloro-1-β-chloroethyl-2-chloromethyl-5-phenyl-2,3-dihydro-1H-1,4-benzodiazepine.

21. A compound as defined in claim 1 which is 7,8-dimethoxy-1-methyl-2-hydroxymethyl-5-(3,4-dimehoxyphenyl)-2,3-dihydro-1H-1,4-benzodiazepine.

22. A compound as defined in claim 1 which is 7-chloro-1-methyl-2-(hydroxymethyl)-5-(2-chlorophenyl)-2,3-dihydro-1H-1,4-benzodiazepine.

* * * * *